(12) United States Patent
Sung et al.

(10) Patent No.: US 8,762,073 B2
(45) Date of Patent: *Jun. 24, 2014

(54) TRANSCRIPT MAPPING METHOD

(75) Inventors: Wing Kin Ken Sung, Singapore (SG); Yijun Ruan, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 13/183,712

(22) Filed: Jul. 15, 2011

(65) Prior Publication Data

US 2012/0016595 A1    Jan. 19, 2012

Related U.S. Application Data

(62) Division of application No. 10/939,592, filed on Sep. 13, 2004, now Pat. No. 8,005,621.

(51) Int. Cl.
*G01N 33/50* (2006.01)

(52) U.S. Cl.
USPC .......................................................... 702/19

(58) Field of Classification Search
None
See application file for complete search history.

(56) References Cited

FOREIGN PATENT DOCUMENTS

WO    WO 2004/015085    *    2/2004

OTHER PUBLICATIONS

Sadakane et al. (Genome Informatics, vol. 12, pp. 175-183, 2001).*
Wei et al. (PNAS, vol. 101, pp. 11701-11706, Aug. 2004).*
Hashimoto et al. (5'-end SAGE for the analysis of transcriptional start sites, Nature Biotechnology, published online Aug. 8, 2004, vol. 22, No. 9, pp. 1146-1149).*

* cited by examiner

*Primary Examiner* — Jason Sims
(74) *Attorney, Agent, or Firm* — Axis Intellectual Capital Pte Ltd

(57) ABSTRACT

A transcript mapping method according to an embodiment of the invention is described hereinafter and combines short tag based (SAGE and MPSS) efficiency with the accuracy of full-length cDNA (flcDNA) for comprehensive characterization of transcriptomes. This method is also referred to as Gene Identification Signature (GIS) analysis. In this method, the 5' and 3' ends of full-length cDNA clones are initially extracted into a ditag structure, with the ditag concatemers of the ditag being subsequently sequenced in an efficient manner, and finally mapped to the genome for defining the gene structure. As a GIS ditag represents the 5' and 3' ends of a transcript, it is more informative than SAGE and MPSS tags. Segment lengths between 5' and 3' tag pairs are obtainable including orientation, ordering and chromosome family for efficient transcript mapping and gene location identification. Furthermore, a compressed suffix array (CSA) is used for indexing the genome sequence for improve mapping speed and to reduce computational memory requirements.

18 Claims, 6 Drawing Sheets

Algorithm Find_Sites (5' sites)
Input: A DNA segment P[1..m], a genome G[1..n], and a threshold $minlength_5$ of minimum contiguous exact match.
Output: A set of 5' sites.

for i = $minlength_5$ downto 1 do
Given the occurrence range of P[i+1..$minlength_5$], we find the occurrence range of P[i..$minlength_5$] by Backward search (Lemma 2).
Extend and report all the occurrences of P[1..$minlength_5$]
for i = 2 to $boundary_5$ − $minlength_5$ + 1 do
for j= $minlength_5$+1 to i+$minlength_5$-1 do
Given the occurrence range of P[i..j-1], we find the occurrence range of P[i..j] by Forward search (Lemma 1).
Extend and report all occurrences of P[i..i+$minlength_5$-1]

End Find_Sites (5' sites)

FIG. 4

Algorithm Match_Sites_1
Input: A set of 5' sites and 3' sites.
Output: A set of occurring segments (feasible gene locations).

Sort the 5' sites in ascending order and let A[1], A[2], ..., A[p] be the list of 5' sites.
Sort the 3' sites in ascending order and let B[1], B[2], ..., B[q] be the list of 3' sites.
Let i=1 and j=1.
while (i ≤ p and j ≤ q) do
if (A[i]>B[j]) then
j = j + 1;
elseif (B[j]-A[i] ≤ *maxlength*)
report (A[i], B[j]) as an occurring segment and j=j+1;
else
i = i + 1;

End Match_Sites_1

FIG. 5

Algorithm Match_Sites_2
Input: A set of 5' sites and 3' sites.
Output: A set of occurring segments.

Let i=1 and j=1.

if ($count_5 \ll count_3$) then
    while (i ≤ p) do
        find 3' site located within *maxlength* downstream from A[i]
        report found 3' site and A[i] as an occurring segment
        i = i + 1;;
elseif ($count_5 \gg count_3$)
    while (j ≤ q) do
        find 5' site located within *maxlength* upstream from B[j]
        report found 5' site and B[j] as an occurring segment
        j = j + 1;;
else
    try Match_Sites_1

End Match_Sites_2

FIG. 6

TRANSCRIPT MAPPING METHOD

CROSS REFERENCE TO RELATED APPLICATION

This application is a divisional application of currently pending U.S. application Ser. No. 10/939,592, filed Sep. 13, 2004.

FIELD OF INVENTION

The present invention relates generally to a transcript mapping method. In particular, the invention relates to a transcript mapping method for mapping from a transcript to a compressed suffix array indexed genome sequence.

BACKGROUND

Since the completion of the genome sequences for human and several other organisms, attention has been drawn towards annotation of genomes for functional elements including gene coding transcript units and regulatory cis-acting elements that modulate gene expression levels.

Currently there are three main approaches for genome annotation. The first approach uses existing transcript data to identify gene-coding regions in the genomes, the second approach uses computational algorithms to statistically predict genes and regulatory elements and the third approach compares genomic sequences from other vertebrates for conserved regions based on the view that functional elements in genomes are conserved during evolution.

Despite considerable success, these approaches are unsatisfactory for determining the complete and precise content of all functional elements in the human genome. As a result, a complete list of genes in the human genome is still unavailable. In particular, all the low abundant and cell specific genes have not been identified. Many gene models suggest that the current genome annotation is incorrect, particularly regarding where the transcription starts and ends.

All the gene predictions have to be validated by experimental means and the prospective genes are required to be cloned in full-length for further functional studies. It is therefore clear that many challenges surround the field of human genome annotation.

One of the challenges is the identification of all genes and all transcripts expressed from the genes in human and model organisms. In the annotation of genes, full-length cDNA cloning and sequencing is the most conclusive and is viewed as the gold standard for the analysis of transcripts. However, this approach is expensive and slow when applied to a large number of transcripts across a large number of species and biological conditions. There are short tag based approaches such as SAGE (serial analysis of gene expression) and MPSS (massively parallel signature sequence). These short tag based methods extract a 14-20 bp signature for representing each transcript. Though this approach is efficient in tagging and counting transcripts in a given transcriptome, the specificity of the tags is often poor and the information yielded regarding transcript structures are frequently incomplete and ambiguous.

Gene Identification Signature (GIS) ditag sequences, obtained by extracting interlinked 5' and 3' ends of full-length cDNA clones into a ditag structure, provide substantial tag specificity. However, there are no existing computer algorithms that are readily applicable for mapping the GISditag sequences to genome. In the past, SAGE and MPSS tags were analyzed using a two-step approach. The tags were first matched to cDNA sequences and then to the genome. In this approach, novel transcripts that did not exist in cDNA databases would not be mapped. The two most often used sequence alignment tools, BLAST (basic local alignment search tool) and BLAT (BLAST-like alignment tool), are not designed for short tag sequences and often leads to poor or incorrect results.

Hence, this clearly affirms a need for an improved transcript mapping method.

SUMMARY

A transcript mapping method according to an embodiment of the invention is described hereinafter and combines short tag based (SAGE and MPSS) efficiency with the accuracy of full-length cDNA (flcDNA) for comprehensive characterization of transcriptomes. This method is also referred to as Gene Identification Signature (GIS) analysis. In this method, the 5' and 3' ends of full-length cDNA clones are initially extracted into a ditag structure, with the ditag concatemers of the ditag being subsequently sequenced in an efficient manner, and finally mapped to the genome for defining the gene structure. In the GIS analysis, each sequence read reveals approximately 15 ditags representing 15 transcripts. This approach increases efficiency by at least 30-folds for identifying and quantifying full-length transcripts compared to the current flcDNA cloning and sequencing approaches. Because each GISditag sequence contains 36 base pairs (bp) to represent the beginning and the end of a transcript, the specificity of mapping tag-to-genome is greatly increased compared to the 14-21 bp SAGE and MPSS tags. In addition, as a GISditag represents the 5' and 3' ends of a transcript, it is more informative than SAGE and MPSS tags.

To accommodate the GISditag data, a Suffix Array based Tag to Genome (SAT2G) algorithm is used for mapping the GISditag sequences to a genome sequence built and indexed on an advanced data structure Compressed Suffix Array (CSA).

Therefore, in accordance with a first aspect of the invention, there is disclosed a transcript mapping method comprising the steps of:

obtaining a 5' terminal tag and a 3' terminal tag from a transcript of a gene;

matching the 5' terminal tag to at least a portion of a genome sequence to thereby identify at least one 5' site therefrom, each of the at least one 5' site having a sequence matching the 5' terminal tag;

matching the 3' terminal tag to at least a portion of the genome sequence to thereby identify at least one 3' site therefrom, each of the at least one 5' site having a sequence matching the 5' terminal tag;

identifying at least one occurring segment, each of the at least one occurring segment being a sequence segment along the genome sequence extending from one of the at least one 5' site to one of the at least one 3' site, each of the at least one occurring segment having a sequence length; and identifying at least one feasible gene location, each of the feasible gene location being one of the at least one occurring segment having a sequence length not exceeding that of a predefined gene length.

In accordance with a second aspect of the invention, there is disclosed a transcript mapping system comprising:

means for obtaining a 5' terminal tag and a 3' terminal tag from a transcript of a gene;

means for matching the 5' terminal tag to at least a portion of a genome sequence to thereby identify at least one 5' site therefrom, each of the at least one 5' site having a sequence matching the 5' terminal tag;

means for matching the 3' terminal tag to at least a portion of the genome sequence to thereby identify at least one 3' site therefrom, each of the at least one 3' site having a sequence matching the 3' terminal tag;

means for identifying at least one occurring segment, each of the at least one occurring segment being a sequence segment along the genome sequence extending from one of the at least one 5' site to one of the at least one 3' site, each of the at least one occurring segment having a sequence length; and means for identifying at least one feasible gene location, each of the feasible gene location being one of the at least one occurring segment having a sequence length not exceeding that of a predefined gene length.

In accordance with a third aspect of the invention, there is disclosed a transcript mapping method comprising the steps of:

obtaining a 5' terminal tag and a 3' terminal tag from a transcript of a gene;

matching the 5' terminal tag to at least a portion of a genome sequence to thereby identify at least one 5' site therefrom, each of the at least one 5' site having a sequence matching the 5' terminal tag;

matching the 3' terminal tag to at least a portion of the genome sequence to thereby identify at least one 3' site therefrom, each of the at least one 5' site having a sequence matching the 5' terminal tag;

identifying at least one occurring segment, each of the at least one occurring segment being a sequence segment along the genome sequence extending from one of the at least one 5' site to one of the at least one 3' site, each of the at least one occurring segment having a sequence length; and identifying at least one feasible gene location from the at least one occurring segment, each of the at least one feasible gene location being one of the at least one occurring segment with at least one of the sequence length thereof not exceeding that of the predefined gene length, the sequence order thereof and of the at least one 5' site and one of the at least one 3' site corresponding thereto in accordance with a 5'-occurring segment-3' structure matching the sequence order of the corresponding portion of the genome sequence, the 5' site and one of the at least one 5' site and one of the at least one 3' site corresponding thereto having a 5'-3' orientation, and one of the at least one 5' site and one of the at least one 3' site corresponding to each of the occurring segment being located within the same chromosome.

BRIEF DESCRIPTION OF THE DRAWINGS

Embodiments of the invention are described hereinafter with reference to the following drawings, in which:

FIG. 4 shows a pseudo code "Find_Sites" of the transcript mapping method of FIG. 2 for forward and reverse searching of 5' sites and 3' sites from a genome sequence; and FIG. 5 shows a pseudo code "Match_sites_1" of the transcript mapping method of FIG. 2 for identifying the sequence length of an occurring segment, the sequence length being subsequently compared with a predefined length for identifying of a feasible gene location therefrom; and FIG. 6 shows a pseudo code "Match_sites_2" of the transcript mapping method of FIG. 2 for identifying an occurring segment when a disparity condition is met wherefrom a feasible gene location is subsequently obtained.

DETAILED DESCRIPTION

A transcript mapping method is described hereinafter for addressing the foregoing problems.

Complete genome annotation relies on precise identification of transcription units bounded by a transcription initiation site (TIS) and a polyadenylation site (PAS). To facilitate this, a pair of complementary methods, namely 5'LongSAGE (long serial analysis of gene expression) and 3'LongSAGE, was developed. These methods are based on the original SAGE (serial analysis of gene expression) and LongSAGE methods that utilize typical full-length cDNA cloning technologies to enable high-throughput extraction of the first and the last 20 base pairs (bp) of each transcript. Mapping of 5' and 3' LongSAGE tags to the genome allows the localization of the TIS and the PAS.

However, matching of 5' and 3' tags derived from same transcripts in genome sequences are not always straightforward and can sometimes be very ambiguous. A solution is to clone the 5' and 3' tags of the same transcript by inter-linking the 5' and 3' tags. To achieve this, a specially designed device comprising cloning adapters and a vector links the 5' tag and the 3' tag derived from the same transcript into a ditag.

Figure 1:
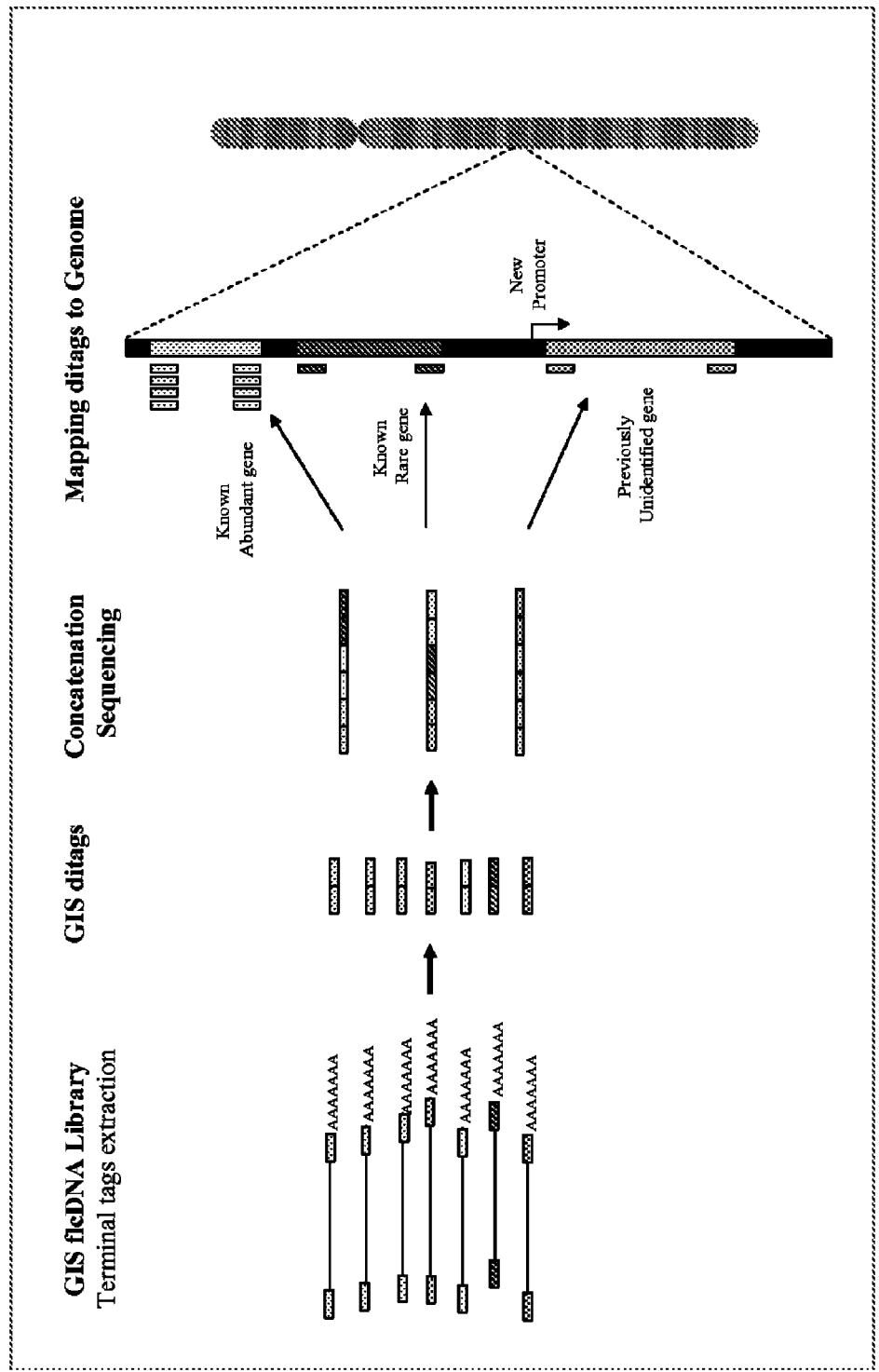
FIG. 1 shows a schematic diagram of a 5' and 3' terminal tags SAGE technique for use in genome annotation.

A plurality of ditags can be concatenated for cloning and sequencing, with each ditag representing an individual transcript. Unlike single tag sequences, the paired ditag sequences can be specifically multiplied with a frame of transcripts being precisely definable when being mapped to the genome sequences. This approach, named Gene Identification Signature (GIS) analysis, can accurately map the 5' and 3' ends of transcription units encoded by genes as shown in FIG. 1.

In the GIS analysis, the conventional cap-trapper method is applied to enrich a full-length cDNA and incorporated adapter sequences that bear an MmeI restriction site at each end of the cDNA fragments. The cDNA fragments are then cloned in a cloning vector to construct a GIS flcDNA (full-length cDNA) library. The plasmid prepared from the library is digested by MmeI (a type II restriction enzyme) and cleaved 20 bp downstream of its binding site. After digestion, the flcDNA inserts of the library were dropped from the plasmid to leave 18 bp signatures of 5' and 3' ends with the learned cloning vector. Re-circling the vector would create a GIS single ditag library. The ditags of the library were then sliced out and purified for concatenating and cloning to generate the final GIS ditag library for sequence analysis. Typically, each sequence read of the GIS ditag clones reveals 15 ditags. Each unit of the ditag sequence contains 18 bp of 5' and 18 bp of 3' signatures with a 12 bp spacer to separate one ditag sequence from another.

Mapping ditags to the genome is akin to searching occurrences of a pattern in the genome sequence. Approaches for pattern searching include the conventional BLAST (basic local alignment search tool) and BLAT (BLAST-like alignment tool) method. Both the BLAST and BLAT methods are very slow because each thereof requires a pattern to be searched by scanning through the whole genome. Moreover, conventional full-text indexing is usually employed if exact occurrences of a pattern with a small mismatch margin are required. Efficient full-text indexing data-structures include a suffix tree and a suffix array.

A suffix tree is a tree-like data-structure having branches stemming from a root with each branch terminating at a leaf that encodes a suffix of the genome sequence. The suffix array is a sorted sequence of all suffices of the genome according to lexicographic order. The suffix array is represented as an array SA[i] where i=1 . . . n and that SA[i]=j means that the j-suffix (suffix starting from character j) is the i-th smallest suffix in the lexicographic order.

Both the suffix tree and the suffix array allow for fast pattern searching. Given a pattern of length x, its occurrences in the genome G[1 . . . n] can be reported in O(x) time and O(x log n) time for the suffix tree and the suffix array respectively. Although the query time is fast, it is not always feasible to build the suffix tree or the suffix array due to large space requirements thereof. For example, for a mouse genome, the suffix tree and the suffix array require 40 Gigabytes (GB) and 13 GB respectively. Such memory requirement far exceeds the memory space capacity of ordinary computers. To solve the memory space problem, we apply the space-efficient compressed suffix array (CSA) indexing data structure. CSA is a compressed form of the suffix array. It can be built efficiently without need for enormous memory requirements using known algorithms. Also, the built CSA is very small. For example, a CSA for the mouse genome (mm3) occupies approximately 1.3 GB. Additionally, CSA is also able to support searching efficiently. Searching a pattern of length x requires only O(x log n) time.

Figure 2:
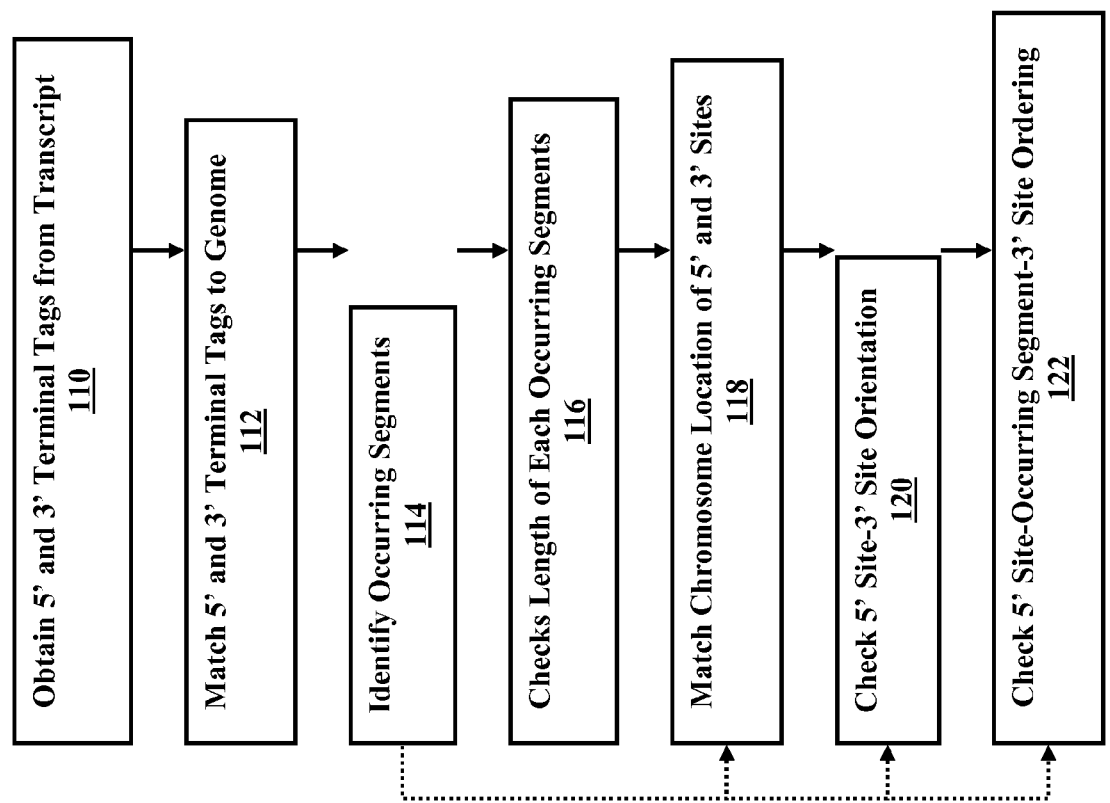
FIG. 2 shows a process flow chart of a transcript mapping method according to an embodiment of the invention.

A first embodiment of the invention, a transcript mapping method 20 is described with reference to FIG. 2, which shows a process flow chart of the transcript mapping method 100. The transcript mapping method 100 is for application to a transcript obtained from a gene. The transcript mapping method 100 is preferably implemented using a computer-based system. In a step 110 of the transcript mapping method 100, a 5' terminal tag 24 and a 3' terminal tag 26 are obtained from the transcript.

Figure 3:
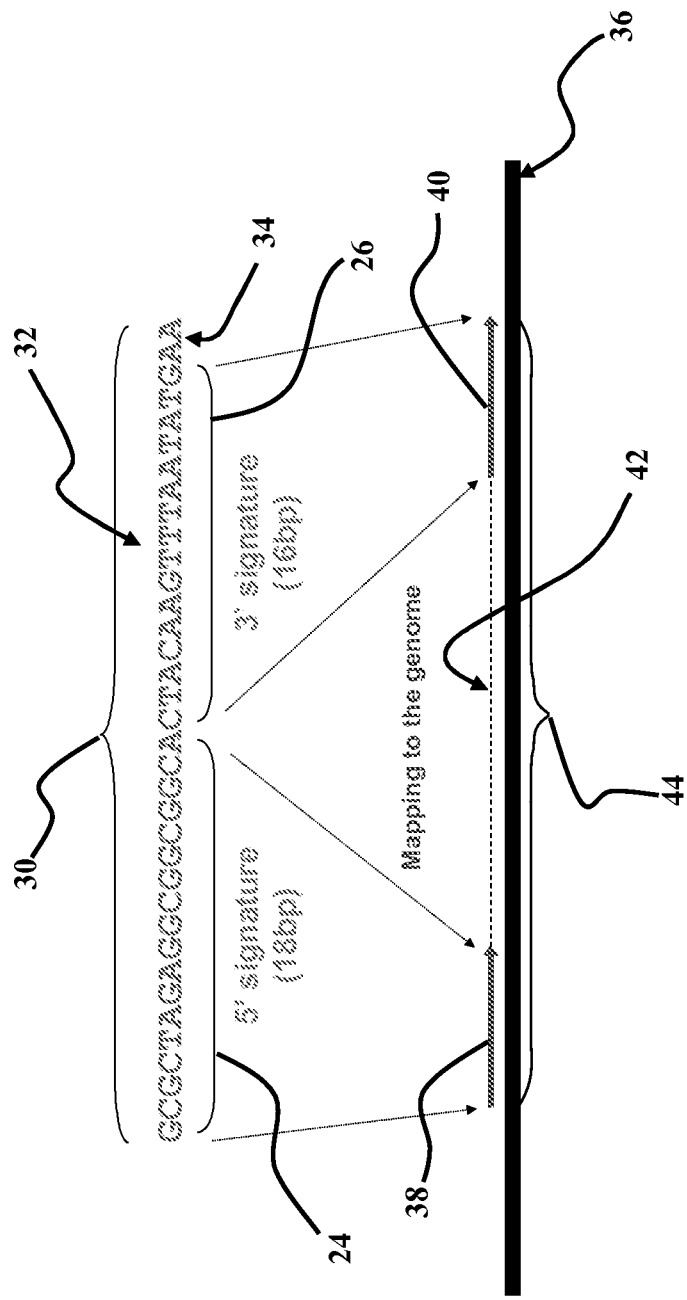
FIG. 3 shows a schematic diagram of a GIS ditag for application of the transcript mapping technique of FIG. 2 thereto.

In combination, the 5' terminal tag 24 (GCGCTAGAG-GCGGCGGCA (SEQ ID NO.: 1)) and the 3' terminal tag 26 (CTACAAGTTTAATATGAA (SEQ ID NO.: 2)) forms a GIS ditag 30 (GCGCTAGAGGCGGCGGCACTACAAGTT-TAATATGAA (SEQ ID NO.: 3)) as described above and as shown in FIG. 3. The GIS ditag 30 has a ditag length 32 of 36 bp with 18 bp nucleotide sequence being derived from the 5' terminal tag 24 and another 18 bp of nucleotide sequence being derived from the 3' terminal tag 26. Due to some enzymatic variations during molecular cloning, the ditag length 32 of the GIS ditag 30 may vary from 34 bp to 38 bp.

This variation often occurs proximate to the extremities of the 5' terminal tag 24 and the 3' terminal tag 26 with the internal nucleotides remaining structurally conserved. In the 3' terminal tag 26, two residual nucleotides 34 (AA) are retained during poly-A tail removal therefrom. The AA residual nucleotides 34 are subsequently for use as an orientation indicator. Therefore, only 16 bp of the 3' terminal tag 26 in the GIS ditag 30 is usable for mapping to a genome sequence 36.

Following the step 110, each of the 5' terminal tag 24 and the 3' terminal tag 26 is matched to the genome sequence 36 in a step 112. In the step 112, 5' sites 38 and 3' sites 40 are identified when the 5' terminal tag 24 and the 3' terminal tag 26 are respectively matched to the genome sequence 36. Each of the 5' sites 38 and each of the 3' sites 40 is a portion of the genome sequence 36 that has a sequence that substantially matches the 5' terminal tag 24 and the 3' terminal tag 26 respectively.

In a step 114, at least one occurring segment 42 is identified from the genome sequence 36. Each of the at least one occurring segment 42 is a sequence segment along the genome sequence 36 situated between one 5' site 38 and one 3' site 40. Each of the at least one occurring segment 42 has a sequence length 44.

Given the GIS ditag 30 (P) for the transcript (R), the computational problem of locating R in the genome sequence 36 (G) is referred to as a transcript location identification problem. Therefore, given G[1 . . . n] and P[1 . . . m], the occurring segment 42 is identified as being a feasible gene location of P when: the sequence length 44 (j-i) is smaller than the predefined gene length (maxlength), which is typically less than 1 million base pairs in length for known genes; the 5' terminal tag 24 and the 3' terminal tag 26 are longer than predefined $minlength_5$ and $minlength_3$ respectively (where $minlength_5$=16 bp and $minlength_3$=14 bp); and the 5' terminal tag 24 and the 3' terminal tag 26 of R are the substrings of P[1 . . . $boundary_5$] and P[$boundary_3$ . . . m] respectively (where $boundary_5$=19 and $boundary_3$=18).

The genome sequence 36 is preferably indexed using a compressed suffix array (CSA). The 5' terminal tag 24 and the 3' terminal tag are matched to the genome sequence 36 preferably by applying binary search to the compressed suffix array. The binary search for matching the 5' terminal tag 24 and the 3' terminal tag 26 are dependent on two lemmas, namely, lemma 1 for performing a forward search on the compressed suffix array and lemma 2 for performing a reverse search on the compressed suffix array.

Lemma 1 (forward search): given the CSA for the genome G[1 . . . n] and a set of occurrences of a pattern Q in G, for any base c∈{adenine (A), cytosine (C), guanine (G), thymine (T)}, a set of occurrences of the pattern Qc is obtainable in O(log n) time. A forward binary search is achieved by modifying a conventional binary search algorithm to use values in the compressed suffix array and suffix array instead of explicit text for the suffixes in the genome sequence 36 when comparing with pattern Q in the binary search.

Lemma 2 (reverse search): given the CSA for the genome G[1 . . . n] and a set of occurrences of a pattern Q in G, for any base c∈{A, C, G, T}, we can find the set of occurrences of the pattern cQ using O(log n) time.

The pseudo code "Find_Sites" for both the forward search and the reverse search is shown in FIG. 4. Instead of applying both the forward search and the reverse search in tandem in the step 114, an alternative approach is to apply either only the forward search using lemma 1 or only the reverse search using lemma 2 to the genome sequence 36 for identifying the at least one occurring segment 42.

The GIS ditag 30 may appear in the genome sequence 36 in sense or anti-sense. To address this issue, an index is created for each of the sense genome sequence and the anti-sense genome sequence. Instead of creating two separated indexing arrays, an anti-sense GIS ditag is created. The suffix array is searched twice in the step 110 for each of the 5' terminal tag 24 and the 3' terminal tag 26, once using the sense GIS ditag 30 and a second time using the anti-sense GIS ditag (not shown).

Additionally, the genome sequence 36 is naturally partitioned into chromosomes. This enables a compressed suffix array to be created for the sequence segment of each chromosome. By doing so, 5' sites 38 and 3' sites 40 are obtainable for specific chromosomes instead of the entire genome sequence 36.

Besides the compressed suffix array, a suffix array, a suffix tree, a binary or the like indexing data structure is usable for indexing the genome sequence 36 as above mentioned.

Following the step 114, the 5' sites 38 and the 3' sites 40 undergo a series of checks to identify a feasible gene location. The checks comprises of length, locality, orientation and ordering checks.

In a step 116, the length check is performed by comparing the sequence length 44 of each of the at least one occurring segment 42 with a predefined gene length in a step 116. Initially, the 5' sites 38 and 3' sites 40 are sorted preferably in an ascending order. Next, each of the at least one occurring segment 42 has a sequence length 44 that does not exceed that of the predefined gene length (maxlength) is identified as a potential feasible gene location. The pseudo code "Match_sites_1" for step 116 is shown in FIG. 5.

In a step 118, the locality check is performed whereby the 5' site 38 and the 3' site 40 corresponding to each of the at least one occurring segment 42 are analysed to identify which chromosome each of them are located within. The occurring segment 42 identifies a potential feasible gene location only when the 5' site 38 and the 3' site 40 thereof belongs to the same chromosome.

In a step 120, the orientation check is performed by identifying the orientation of the 5' site 38 and the 3' site 40 that corresponds to each occurring segment 42. The orientation of the 5' site 38 and the 3' site is identifiable by locating the position of the residual nucleotide 34. Preferably, the 5' site 38 and the 3' site 40 should have a 5'-3' orientation for the occurring segment 42 thereof to identify a potential feasible gene location.

In a step 122, the ordering check is performed by comparing each of the occurring segments 42 and the corresponding 5' site 38 and 3' site 40 to the genome sequence 36. Preferably, the ordering of each of the occurring segments 42 and its corresponding 5' site 38 and 3' site 40 should follow a 5'-occurring segment-3' structure for it to be a potential feasible site.

Steps 116-122 of the transcript mapping method can occur in any sequence in combination or independently.

In a situation where the feasible gene location is not found from the GIS ditag 30, the constraints are relaxed to allow at least one mismatch when matching the 3' terminal tag 26 to the genome sequence 36 in the step 112.

Alternatively, the quantity of the 5' sites 38 and the quantity of the 3' sites 40 are initially obtained before the 5' sites 38 and the 3' sites 40 are matched to the genome sequence 36 in the step 112. This enables identification of quantity disparity between the 5' sites 38 and the 3' sites 40, for example, when there only exist less than ten of the 5' sites 38 and more than tens of thousand of the 3' sites 40, or vice versa.

When large quantity disparity between the 5' sites 38 and the 3' sites 40 exists, the transcript mapping method 20 undergoes multiple iterations of redundant mapping to the genome sequence 36. Therefore, a modified approach is required for the transcript mapping method 100 when a large quantity disparity arises. To identify the quantity disparity, a disparity condition is established as:

$$\frac{1}{threshold_{5,3}} \leq \frac{count_5}{count_3} \leq threshold_{5,3}$$

where $count_5$ is the quantity of 5' sites 38, $count_3$ is the quantity of 3' sites 40, and $threshold_{5,3}$ is a pre-defined threshold, for example $threshold_{5,3}$=10,000, for limiting the quantitative disparity between $count_5$ and $count_3$. The CSA enables both $count_5$ and $count_3$ to be obtained without enumerating either any of the 5' sites 38 or any of the 3' sites.

The method described in the pseudo code "Match_sites_2" of FIG. 6 is applied when the above disparity condition is met. In the pseudo code "Match_sites_2", the number of iterations required for mapping to the genome sequence 36 is determined by the smaller one of $count_5$ and $count_3$. For example, should there be only two 5' sites 38, the mapping to or traversal along the genome sequence 36 for obtaining the corresponding one of the 3' sites 40 is only iterated twice, once for each of the two 5' sites 38, for obtaining the occurring segments 42 therefrom.

However, should the above disparity condition be unmet, the quantity disparity between $count_5$ and $count_3$ is not large and therefore the transcript mapping method 100 reverts to the method described in "Match_sites_1" for obtaining the occurring segments 42.

In the foregoing manner, a transcript mapping method is described according to one embodiment of the invention for addressing the foregoing disadvantages of conventional mapping methods. Although only one embodiment of the invention are disclosed, it will be apparent to one skilled in the art in view of this disclosure that numerous changes and/or modification can be made without departing from the scope and spirit of the invention.

The invention claimed is:

1. A computer-based transcript mapping system comprising:
   a computer comprising:
   a first module, implemented on the computer, for matching a 5' terminal tag to at least a portion of a genome sequence to thereby identify at least one 5' site therefrom, the 5' terminal tag obtainable from a transcript, each of the at least one 5' site having a sequence matching the 5' terminal tag;
   a second module, implemented on the computer, for matching a 3' terminal tag to at least a portion of the genome sequence to thereby identify at least one 3' site therefrom, the 3' terminal tag obtainable from the transcript, each of the at least one 3' site having a sequence matching the 3' terminal tag;
   a third module, implemented on the computer, for identifying quantity of the at least one 5' site and for identifying quantity of the at least one 3' site, numerically determining a quantity disparity between the at least one 5' site and the at least one 3' site, determining whether the quantity disparity between the at least one 5' site and the at least one 3' site satisfies a disparity condition, and limiting the quantity disparity between the at least one 5' site and the at least one 3' site in accordance with the disparity condition;
   a fourth module, implemented on the computer, for identifying at least one occurring segment, each of the at least one occurring segment being a sequence segment along the genome sequence extending from one of the at least one 5' site to one of the at least one 3' site, each of the at least one occurring segment having a sequence length;
   a fifth module, implemented on the computer, for identifying at least one feasible gene location, each of the at least one feasible gene location being one of the at least one occurring segment having a sequence length not exceeding that of a predefined gene length; and
   a sixth module, implemented on the computer, for generating a data structure for indexing the genome sequence.

2. The computer-based transcript mapping system as in claim 1, the fourth module for identifying at least one occurring segment further
   for traversing along the genome sequence towards one of the extremities thereof from each of the at least one 5' site for identifying at least one of the at least one 3' site and
   for traversing along the genome sequence towards one of the extremities thereof from each of the at least one 3' site for identifying at least one of the at least one 5' site.

3. The computer-based transcript mapping system as in claim 2, the fifth module for identifying the at least one feasible gene location further
   for terminating traversal along the genome sequence in response to one of the at least one feasible gene location being identified for each of the at least one 5' site.

4. The computer-based transcript mapping system as in claim 1, the fourth module for identifying at least one occurring segment further
   for traversing along the genome sequence towards one of the extremities thereof from each of the at least one 3' site for identifying at least one of the at least one 5' site.

5. The computer-based transcript mapping system as in claim 2, the fifth module for identifying the at least one feasible gene location further
   for terminating traversal along the genome sequence in response to one of the at least one feasible gene location being identified for each of the at least one 3' site.

6. The computer-based transcript mapping system as in claim 1, wherein the 5' terminal tag is formed from a nucleotide sequence with at least 16 base pairs and the 3' terminal tag is formed from a nucleotide sequence with at least 16 base pairs.

7. The computer-based transcript mapping system as in claim 1, wherein the first module matches the 5' terminal tag to a chromosome sequence.

8. The computer-based transcript mapping system as in claim 1, wherein the second module matches the 3' terminal tag to a chromosome sequence.

9. The computer-based transcript mapping system as in claim 1, the fourth module further for traversing along the genome sequence from one extremity to the other extremity, and the fifth module further for terminating traversal along the genome sequence in response to one of the at least one feasible gene location being identified for one of each of the at least one 5' site and each of the at least one 3' site.

10. The computer-based transcript mapping system as in claim 1, wherein the data structure generated by the sixth module is at least one of a tree structure and an ordered array for indexing the genome sequence.

11. The computer-based transcript mapping system as in claim 1, wherein the data structure generated by the sixth module is at least one of a suffix array, a suffix tree, a binary tree and a compressed suffix array for indexing the genome sequence.

12. The computer-based transcript mapping system as in claim 1, the first module further for
at least one of forward traversing and reverse traversing the genome sequence for comparing the 5' terminal tag to at least a portion of the genome sequence to obtain the at least one 5' site.

13. The computer-based transcript mapping system as in claim 1, the second module further for
at least one of forward traversing and reverse traversing the genome sequence for comparing the 3' terminal tag to at least a portion of the genome sequence to obtain the at least one 3' site.

14. The computer-based transcript mapping system as in claim 1, the fifth module further for
comparing sequence order of each of the at least one occurring segment and one of the at least one 5' site and one of the at least one 3' site corresponding thereto to at least a portion of the genome sequence for obtaining the at least one feasible gene location therefrom.

15. The computer-based transcript mapping system as in claim 1, the fifth module further for comparing the sequence order of each of the at least one occurring segment and one of the at least one 5' site and one of the at least one 3' site corresponding thereto being in accordance with a 5'-occurring segment-3' structure.

16. The computer-based transcript mapping system as in claim 1, the fifth module further for
identifying the 5'-3' orientation of each of the at least one occurring segment for obtaining the at least one feasible gene location therefrom.

17. The computer-based transcript mapping system as in claim 1, the fifth module further for identifying a residual AA nucleotide, the residual AA nucleotide constituting a portion of the 3' terminal tag.

18. The computer-based transcript mapping system as in claim 1, the fifth module further for identifying the chromosome wherein each of one of the at least one 5' site and one of the at least one 3' site corresponding to each of the occurring segment is located for identifying the at least one feasible gene location therefrom.

* * * * *

SEQUENCE LISTING

<160> NUMBER OF SEQ ID NOS: 3

<210> SEQ ID NO 1
<211> LENGTH: 18
<212> TYPE: DNA
<213> ORGANISM: Artificial sequence
<220> FEATURE:
<223> OTHER INFORMATION: illustration of a 5' terminal tag of a Gene
      Identification Signature (GIS) ditag in Fig. 3.

<400> SEQUENCE: 1
gcgctagagg cggcggca                                                    18

<210> SEQ ID NO 2
<211> LENGTH: 18
<212> TYPE: DNA

```
<213> ORGANISM: Artificial sequence
<220> FEATURE:
<223> OTHER INFORMATION: illustration of a 3' terminal tag of a Gene
      Identification Signature (GIS) ditag in Fig. 3.

<400> SEQUENCE: 2
ctacaagttt aatatgaa                                                        18

<210> SEQ ID NO 3
<211> LENGTH: 36
<212> TYPE: DNA
<213> ORGANISM: Artificial sequence
<220> FEATURE:
<223> OTHER INFORMATION: illustration of a Gene Identification Signature
      (GIS) ditag in Fig. 3.

<400> SEQUENCE: 3
gcgctagagg cggcggcact acaagtttaa tatgaa                                    36
```